United States Patent
Labyed

(10) Patent No.: US 11,617,567 B2
(45) Date of Patent: *Apr. 4, 2023

(54) QUANTITATIVE ULTRASOUND USING FUNDAMENTAL AND HARMONIC SIGNALS

(71) Applicant: Siemens Medical Solutions USA, Inc., Malvern, PA (US)

(72) Inventor: Yassin Labyed, Carlsbad, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/724,590

(22) Filed: Apr. 20, 2022

(65) Prior Publication Data

US 2022/0240900 A1 Aug. 4, 2022

Related U.S. Application Data

(63) Continuation of application No. 16/358,808, filed on Mar. 20, 2019, now Pat. No. 11,331,078.

(51) Int. Cl.
| | | |
|---|---|---|
| *A61B 8/08* | (2006.01) | |
| *G01S 7/52* | (2006.01) | |
| *A61B 8/00* | (2006.01) | |

(52) U.S. Cl.
CPC ............ *A61B 8/5223* (2013.01); *A61B 8/469* (2013.01); *G01S 7/52036* (2013.01);
(Continued)

(58) Field of Classification Search
None
See application file for complete search history.

(56) References Cited

U.S. PATENT DOCUMENTS

| | | |
|---|---|---|
| 2012/0232388 A1 | 9/2012 | Curra et al. |
| 2017/0273667 A1 | 9/2017 | Labyed |
| 2018/0289323 A1 | 10/2018 | Labyed et al. |

FOREIGN PATENT DOCUMENTS

JP    2016112400 A    6/2016

OTHER PUBLICATIONS

Thuras, A.L. "Extraneous Frequencies Generated in Air Carrying Intense Sound Waves", J.A.S.A. vol. VI, Jan. 1935, 8 pages.
(Continued)

*Primary Examiner* — Colin T. Sakamoto

(57) ABSTRACT

A system and method include control of an ultrasound system transducer to acquire an echo signal power spectrum of a region of tissue for a fundamental frequency band and an echo signal power spectrum of the region of tissue for a harmonic frequency band, wherein a center frequency of the harmonic frequency band is substantially similar to a center frequency of the fundamental frequency band, determination of a first backscatter coefficient based on the echo signal power spectrum of the region of tissue for a fundamental frequency band and an echo signal power spectrum of a reference phantom for the fundamental frequency band, determination of a value representing a second backscatter coefficient and a non-linearity term associated with the region of tissue based on the echo signal power spectrum of the region of tissue for the harmonic frequency band and an echo signal power spectrum of the reference phantom for the harmonic frequency band, determination of the non-linearity term associated with the region of tissue based on the first backscatter coefficient and the value, and display the second backscatter coefficient, the non-linearity term, and a B-mode image of the region of tissue.

18 Claims, 6 Drawing Sheets

(52) U.S. Cl.
CPC ......... *G01S 7/52085* (2013.01); *A61B 8/4494* (2013.01); *A61B 8/48* (2013.01); *A61B 8/56* (2013.01)

(56) References Cited

OTHER PUBLICATIONS

Yao, et al., "Backscatter Coefficient Measurements Using a Reference Phantom to Extract Depth-Dependent Instrumentation Factors", Ultrasonic Imaging 12, University of Wisconsin—Madison, Department of Medical Physics, Radiology and Human Oncology, pp. 58-70, 1990, 13 pages.

Labyed et al., "A theoretical comparison of attenuation measurement techniques from backscattered ultrasound echoes", Department of Electrical Engineering, Iowa State University, Jan. 2011, 9 pages.

Lin, Steven C et al., "Noninvasive Diagnosis of Nonalcoholic Fatty Liver Disease and Quantification of Liver Fat Using a New Quantitative Ultrasound Technique", Clinical Gastroenterology and Hepatology, 2015, 16 pages.

Li, et al., "Harmonic ultrasound fields through layered liquid media", IEEE Transactions on Ultrasonics, Ferroelectrics and Frequency Control, vol. 51, No. 2, Feb. 1, 2004, pp. 146-152.

Radulescu, et al., "Calibration of ultrasonic hydrophone probes up to 100 MHz using time gating frequency analysis and finite amplitude waves", Ultrasonics, IPC Science and Technology Press Ltd. Guildford, vol. 41, No. 4, Jun. 1, 2003, pp. 247-254.

International Search Report received in Corresponding application No. PCT/US2020/16912, dated Jun. 29, 2020.

Krishnan, et al., "A Two-parameter Meter for Ultrasonic Tissue Characterization with Harmonic Imaging", arXiv Medical Physics, Dec. 2017.

Insana, et al., "Parameteric Ultrasound Imaging from Backscatter Coefficient Measurements: Image Formation and Interpretation" Ultrasonic Imaging 12, 245-267, 1990.

| Phantom Type | Scan Settings | Fundamental Frequency Band Power Spectrum Data | Harmonic Frequency Band Power Spectrum data |
|---|---|---|---|
| Thorax | Settings_1A | FF_T_1A | HF_T_1A |
| Thorax | Settings_1B | FF_T_1B | HF_T_1B |
| Thorax | Settings_2 | FF_T_2 | HF_T_2 |
| Abdomen | Settings_1B | FF_A_1B | HF_A_1B |
| Abdomen | Settings_3 | FF_A_3 | HF_A_3 |
| Pelvis | Settings_1A | FF_P_1A | HF_P_1A |
| Pelvis | Settings_1B | FF_P_1B | HF_P_1B |
| Pelvis | Settings_3 | FF_P_3 | HF_P_13 |

*FIG. 4*

QUANTITATIVE ULTRASOUND USING FUNDAMENTAL AND HARMONIC SIGNALS

CROSS-REFERENCE TO RELATED APPLICATIONS

This is a continuation application of U.S. patent application Ser. No. 16/358,808, filed Mar. 20, 2019 and entitled "Quantitative Ultrasound Using Fundamental and Harmonic Signals", the contents of which are incorporated herein by reference for all purposes.

BACKGROUND

A conventional ultrasound imaging system creates an internal image (i.e., a B-mode image) of a volume by detecting acoustic impedance discontinuities within the volume. More specifically, conventional ultrasound imaging involves transmitting ultrasound beams into a volume and detecting the returned signals which reflect from acoustic impedance discontinuities within the volume. Since different materials typically exhibit different acoustic impedances, the detected acoustic impedance discontinuities represent the locations of different materials within the volume.

The above-described B-mode images depict qualitative features in tissue but do not directly provide quantitative information regarding the tissue. Quantitative ultrasound systems, on the other hand, can determine an attenuation coefficient (AC) and a backscatter coefficient (BSC) of a Region of Interest (ROI). The AC is a measure of the ultrasound energy loss in tissue and the BSC is a measure of the ultrasound energy returned from tissue. Quantitative ultrasound values such as these are helpful in characterizing properties of tissue such as stiffness and fat fraction. Additional quantitative ultrasound measures would further assist these characterizations.

Determination of an AC and a BSC require compensation for system effects of the acquiring ultrasound system. These effects include transmit-pulse power, transducer sensitivity, beam-focusing pattern, and depth-dependent receiver gain. Conventionally, compensation includes dividing the echo signal power spectrum of a tissue sample in the fundamental frequency band by the echo signal power spectrum of a well-characterized reference phantom in the fundamental frequency band from the same depth. The resulting quotient is a normalized spectrum that depends on the attenuation and backscatter properties of the tissue sample and of the reference phantom. Since the properties of the reference phantom are known, the AC and the BSC of the tissue sample can be derived from the normalized spectrum.

One drawback of the foregoing determination is the need to acquire reference phantom data at the time of the clinical scan. This additional acquisition hinders workflow and patient throughput. Moreover, the accuracy of such determinations has been seen as lacking in many scenarios. The foregoing determination also fails to provide other potentially-useful quantitative measures, such as tissue non-linearity.

BRIEF DESCRIPTION OF THE DRAWINGS

The construction and usage of embodiments will become apparent from consideration of the following specification as illustrated in the accompanying drawings, in which like reference numerals designate like parts, and wherein:

FIG. 4 is a tabular representation of data for determining reference phantom calibration data according to some embodiments;

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide efficient and accurate determination of quantitative ultrasound values. More specifically, some embodiments provide an inventive system to determine an AC and a BSC based on echo signal power spectra from a harmonic frequency band. Using the harmonic frequency band is clinically more desirable. The clinical benefit of using harmonic signals is improved repeatability and reproducibility of QUS estimates from reduced reverberation, clutter noise, and phase aberration.

Such embodiments may utilize pre-stored echo signal power spectra (or RF or IQ signal data from which power spectra may be computed) of a well-characterized reference phantom in the harmonic frequency band, eliminating the need to acquire calibration data at or near to the time of clinical data acquisition.

Some embodiments advantageously determine quantitative values of tissue non-linearity. In contrast, the conventional systems described above assume that the non-linearity of the reference phantom is substantially equal to the non-linearity of the tissue in the ROI.

Figure 1:
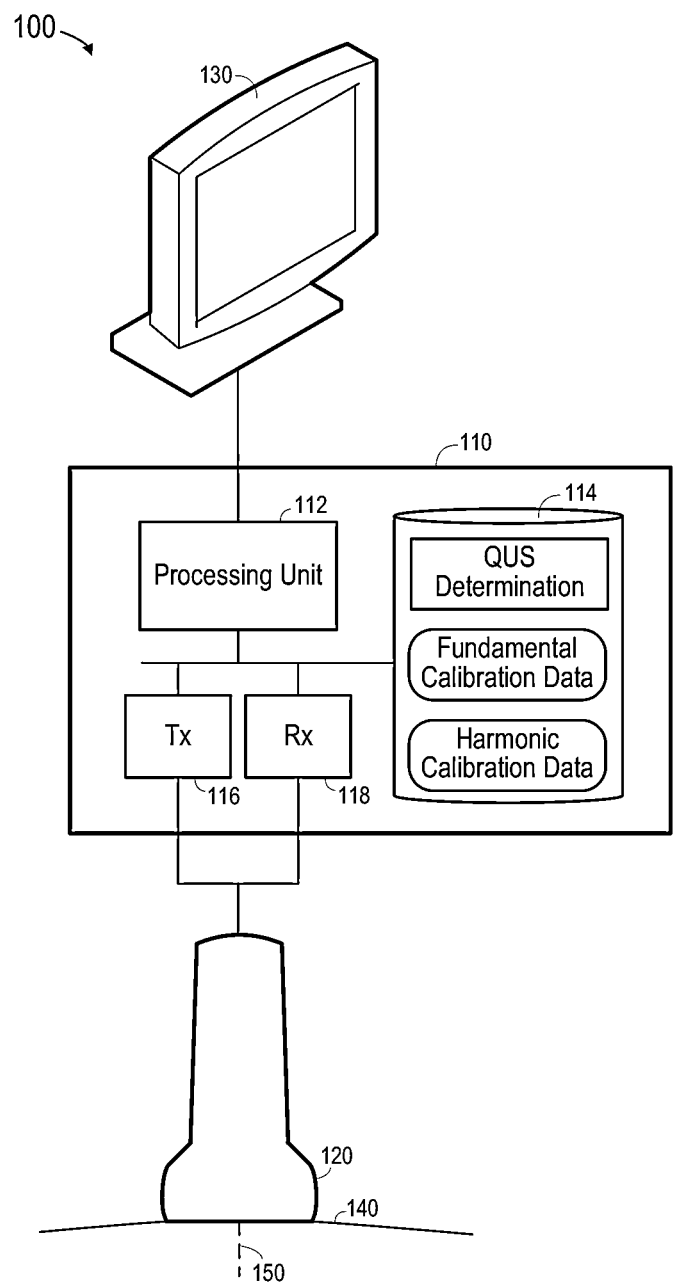
FIG. 1 is a block diagram of a quantitative ultrasound system according to some embodiments.

FIG. 1 illustrates an implementation according to some embodiments. System 100 includes ultrasound unit 110, ultrasound transducer 120 and display 130. Volume 140 may comprise a human body but embodiments are not limited thereto. Ultrasound transducer 100 may comprise any suitable ultrasound transducer, such as but not limited to a phased-array, linear or convex ultrasound transducer.

Generally, processing unit 112 of unit 110 may execute program code to control transducer 120 to transmit ultrasound beams into volume 140 and receive acoustic radio-frequency signals therefrom. Processing unit 112 of unit 110 may execute program code to generate images and/or determine quantitative ultrasound values based on the received signals. The images and/or determined values may be displayed to a technician on display 130.

According to some embodiments, a technician operates system 100 to acquire echo signal power spectra of a harmonic frequency band from a ROI of volume 140. Acquisition may include acquiring RF or IQ signals and computing echo signal power spectra of the harmonic frequency band therefrom. The acquisition is performed using first scan settings, which may include particular values of frequency, F-number/aperture size, focus and apodization function parameters. Transducer 120 operates in conjunction with transmission unit 116 to transmit ultrasound beams into the ROI and receiver unit 118 operates in conjunction with transducer 120 to receive reflected signals in the harmonic frequency band from the ROI according to the scan settings.

Next, harmonic calibration data corresponding to the first scan settings is retrieved from storage 114. The harmonic calibration data may comprise an echo signal power spectrum of a harmonic frequency band (or data from which the echo signal power spectrum may be derived) acquired from a reference phantom using scan settings which are identical or substantially similar to the first scan settings. Acquisition and storage of the harmonic calibration data is described in detail below.

The echo signal power spectra acquired from volume 140 is normalized by dividing the echo signal power spectra by the stored echo signal power spectrum. The result is a normalized spectrum that depends only on the attenuation and backscatter properties of the tissues of the ROI and the reference phantom. Since the attenuation and backscatter properties of the reference phantom are known, the AC and the BSC of the tissues can be derived from the normalized spectrum as will be described in detail below.

According to some embodiments, echo signal power spectra of a fundamental frequency band is also acquired from the ROI of volume 140. The acquisition is performed using second scan settings, which may differ or not from the first scan settings mentioned above. Fundamental calibration data corresponding to the second scan settings is retrieved from storage 114. The fundamental calibration data comprises an echo signal power spectrum of a fundamental frequency band (or, again, RF or IQ data from which the echo power signal spectrum may be derived) acquired from the reference phantom using scan settings which are identical or substantially similar to the second scan settings.

The echo signal power spectra of the fundamental frequency band acquired from volume 140 is normalized by dividing the echo signal power spectra by the fundamental calibration data, resulting in another normalized spectrum that depends only on the attenuation and backscatter properties of the tissues of the ROI and the reference phantom. An AC and a BSC of the tissues can also be derived from this normalized spectrum.

According to some embodiments, a non-linearity of the ROI may be determined based on the BSC derived from the harmonic frequency band data and the BSC derived from the fundamental frequency band data. Such a determination provides improved characterization of the ROI over conventional systems which assume that the non-linearities of the reference phantom and of the ROI are equivalent.

Figure 2:
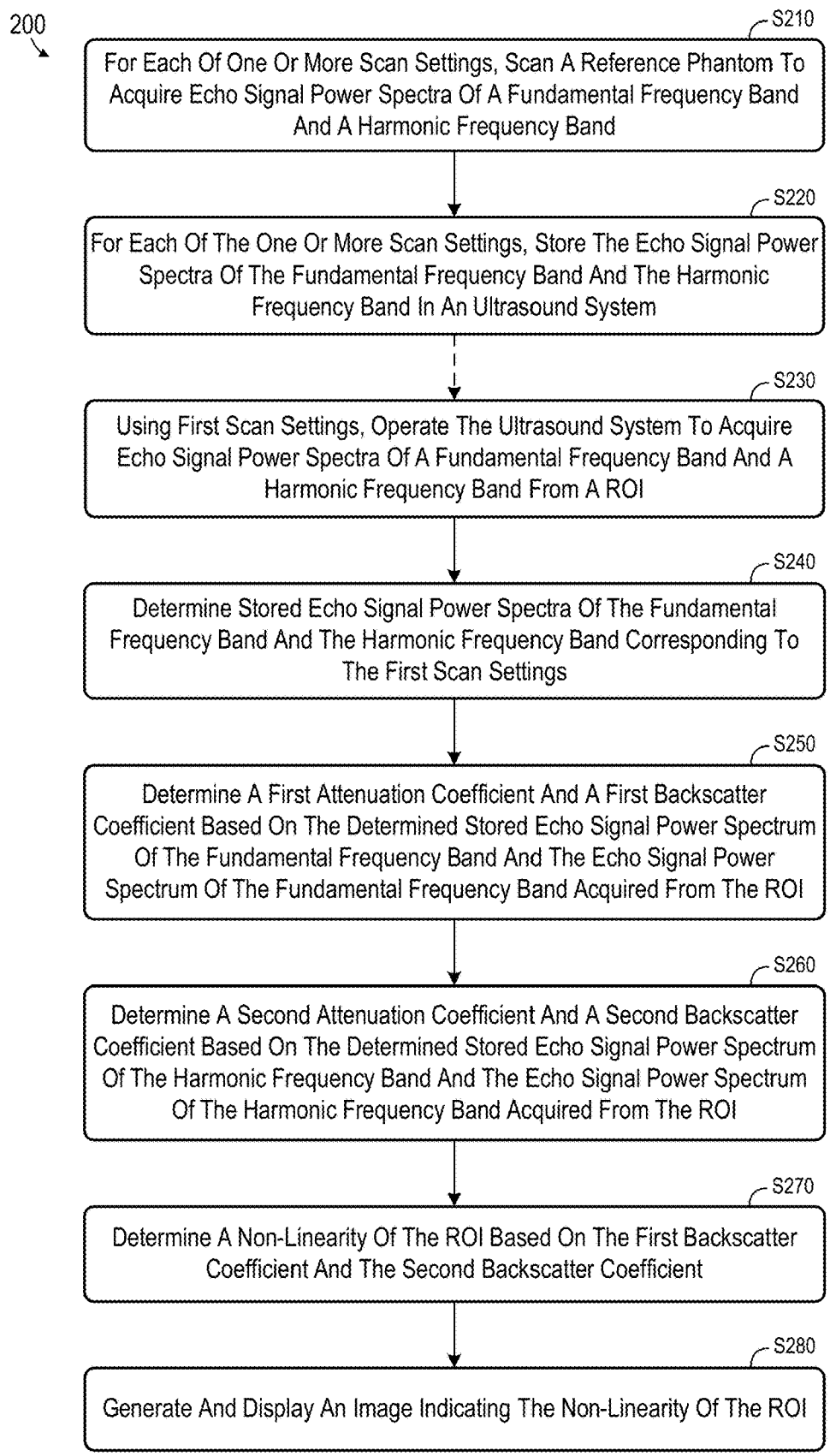
FIG. 2 is a flow diagram of a process to determine quantitative ultrasound values according to some embodiments.

FIG. 2 is a flow diagram of process 200 to determine quantitative ultrasound values according to some embodiments. Process 200 may be executed by elements of system 100, but embodiments are not limited thereto. Process 200 and all other processes mentioned herein may be embodied in processor-executable program code read from one or more of non-transitory computer-readable media, such as a hard disk, volatile or non-volatile random access memory, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S210, a reference phantom is scanned to acquire RF or IQ data and determine an echo signal power spectra of a fundamental frequency band and of a harmonic frequency band therefrom. The reference phantom is scanned used particular scan settings. In some embodiments, additional echo signal power spectra of a fundamental frequency band and of a harmonic frequency band are acquired at S210 using other scan settings.

Figure 3:
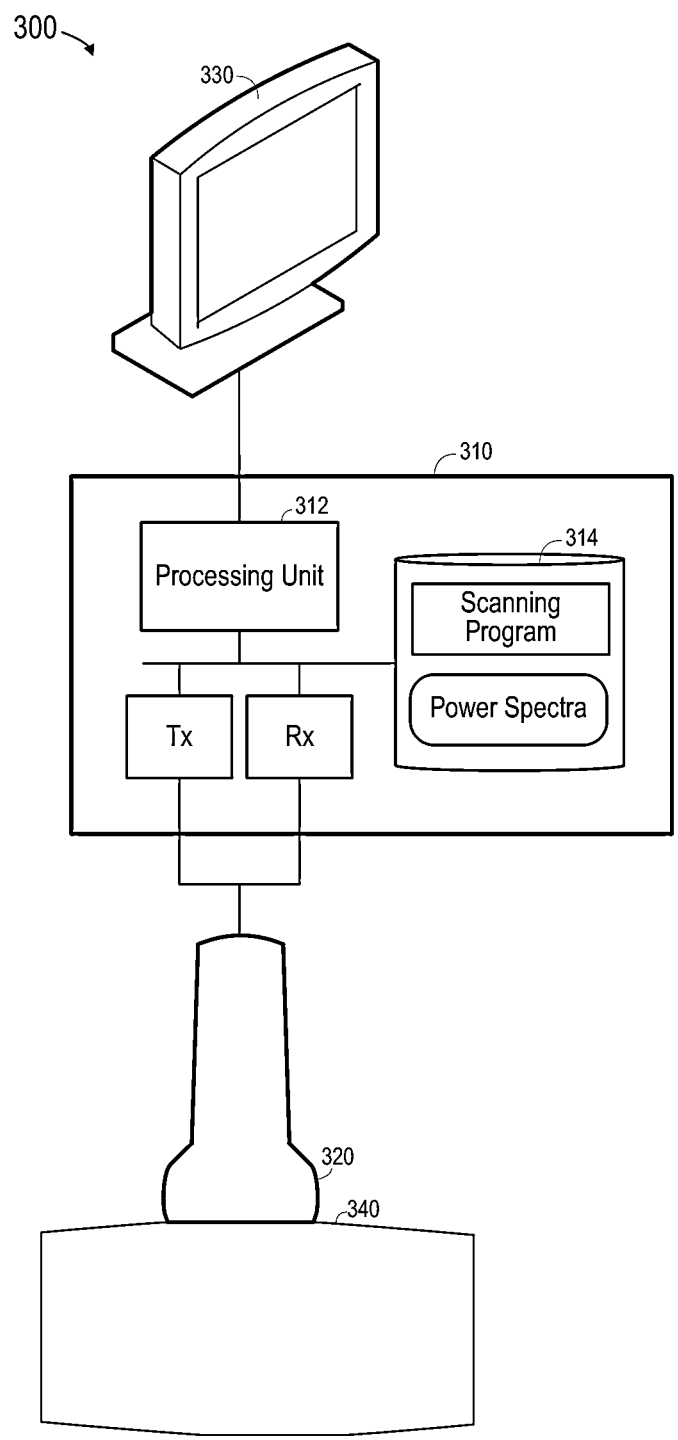
FIG. 3 is a block diagram of an ultrasound system to acquire reference phantom calibration data according to some embodiments.

FIG. 3 illustrates system 300 to perform S210 according to some embodiments. System 300 may be operated by an ultrasound system provider, a phantom provider, or other non-clinical entity. Processing unit 312 of ultrasound unit 310 executes a scanning program of storage 314 to control transducer 320 to transmit signals to and receive signals from phantom 340. Phantom 340 represents an anticipated ROI (e.g., an adult male torso) and ultrasound unit 310 and transducer 320 may comprise production-equivalent versions of ultrasound units and transducers which are anticipated to be used in scanning the anticipated ROI. Storage 314 stores the acquired power spectra.

Next, at S220, the acquired echo signal power spectra of a fundamental frequency band and of a harmonic frequency band are stored in an ultrasound system. In some embodiments, the stored data comprises data from which the echo signal power spectra of a fundamental frequency band and of a harmonic frequency band may be derived. In some examples, the spectra are stored as the above-described fundamental and harmonic calibration data of an ultrasound system to be shipped to a customer. According to some embodiments, the spectra are stored in association with the scan settings used to acquire the respective spectra.

FIG. 4 is a tabular representation of data stored at S220 according to some embodiments. Table 400 associates each acquired power spectrum with a reference phantom and scan settings used to acquire the power spectrum. As shown, more than one type of reference phantom may be scanned at S210. Each reference phantom/scan setting pair is associated with fundamental frequency band power spectrum data and harmonic frequency band power spectrum data. The values of the spectrum data columns may consist of filenames of files including the corresponding spectrum data.

In some embodiments, S210 and S220 are performed during a time period well before clinical use (e.g., before shipping an ultrasound system to a clinic) of the data acquired therein. Accordingly, the dashed arrow between S220 and S230 indicates a passage of time which may be significantly longer than the time between other adjacent steps of process 200.

At S230, for example in a clinical setting, the ultrasound system in which the spectra are stored is operated to acquire echo signal power spectra of a fundamental frequency band and of a harmonic frequency band from a ROI. The acquisition uses first scan settings which were used to generate calibration data of a corresponding reference phantom at S210. In some embodiments, the first scan settings are set as default scan settings of the ultrasound system.

According to some embodiments of S230, the ultrasound system transmits a signal with a 3 MHz center frequency and a frequency bandwidth from 2-4 MHz. The fundamental signal is then received, in the range of 2-4 MHz. To obtain signals in the harmonic frequency band, a signal is transmitted at a 1.5 MHz center frequency and having a bandwidth between 1-2 MHz. The resulting received harmonic signal may exhibit a frequency band of, e.g., double the center frequency, or between 2-4 MHz. According, subsequent calculations of the QUS values are associated with frequencies between 2-4 MHz.

Next, at S240, stored calibration data corresponding to the first scan settings is determined. The determined calibration data consists of echo signal power spectra of the fundamental frequency band and the harmonic frequency band which were acquired using the first scan settings and a reference phantom corresponding to the ROI. For example, S240 may comprise identifying an appropriate reference phantom and scan settings within a row of table 400, and acquiring the stored fundamental and harmonic calibration data files identified within the same row of table 400.

A first AC and a first BSC are determined at S250. The determination is based on the echo signal power spectra of the fundamental frequency band acquired at S230 and the calibration echo signal power spectra of the fundamental frequency band determined at S240. Embodiments are not limited to the following description of the determination at S250.

Initially, each radio-frequency echo line of the ROI is partitioned into several overlapping time-gated windows. The Fourier Transform is applied to every window, and the power spectra of the windows that correspond to the same depth are averaged. The same procedure is performed on the corresponding ROI of the reference phantom. In standard pulse echo imaging, the measured power spectrum in the fundamental frequency band of a windowed region in a statistically homogeneous tissue is given by equation (1):

$$S_s(f,z) = T(f)E_{tx}(f)E_{rx}(f)D(f,z)(f,z)BSC_s(f)e^{-4\alpha_s(f)z} \quad (1)$$

The subscript s represents the sample (i.e., the tissue of the ROI). The distance from the surface of the transducer to the center of a particular time-gated window within the ROI is denoted by z. The frequency is denoted by f. $T(f)$ represents the transfer function of transmit pulse. $E_{tx}(f)$ and $E_{rx}(f)$ represents transducer electro-acoustic and acousto-electric transfer functions, respectively. $D(f,z)$ denotes the effects of diffraction that are related to the transducer geometry and transmit and receive focusing. $\alpha_s(f)$ and $BSC_s(f)$ are the frequency-dependent AC and BSC values of the sample, respectively.

Similarly, the power spectrum of the backscattered signal from the reference phantom is:

$$S_r(f,z) = T(f)E_{tx}(f)E_{rx}(f)D(f,z)BSC_r(f)e^{-4\alpha_r(f)z} \quad (2)$$

Dividing the power spectra of the sample by the power spectra of the reference phantom yields:

$$RS(f, z) = \frac{S_s(f)}{S_r(f)} = \frac{BSC_s(f)e^{-4\alpha_s(f)z}}{BSC_r(f)e^{-4\alpha_r(f)z}} \quad (3)$$

Compensating for the known attenuation and backscatter properties of the reference phantom, equation (3) becomes:

$$RS'(f,z) = BSC_s(f)e^{-4\alpha_s(f)z} \quad (4)$$

Computing the natural logarithm yields:

$$\ln(RS'(f,z)) = \ln(BSC_s(f)) - 4\alpha_s(f)z \quad (5)$$

The attenuation coefficient $\alpha_s(f)$ (np/cm) and the backscatter coefficient $BSC_s$ (1/cm-str) can then be derived from the slope ($-4\alpha_s(f)$) and intercept (ln ($BSC_s(f)$)) of the line that fits equation (5) versus depth z.

A second AC and a second BSC are determined at S260. The determination at S260 is based on the echo signal power spectra of the harmonic frequency band acquired at S230 and the calibration echo signal power spectra of the harmonic frequency band determined at S240. Embodiments are not limited to the following description of the determination at S260.

Using the harmonic frequency band to estimate the AC and BSC requires anew model that accounts for tissue nonlinearity. The second harmonic pressure from a plane wave of $P_0$ at fundamental frequency f is given by:

$$P_h(2f) = KP_0^2(f)\frac{e^{-\alpha_h(2f)z} - e^{-2\alpha_f(f)z}}{2\alpha_f(f) - \alpha_h(2f)} \quad (6)$$

where $\alpha_f(f)$ and $\alpha_h(2f)$ are the attenuation coefficients (np/cm) of the fundamental and harmonic signal respectively, and K is a constant that is proportional to the nonlinearity parameter B/A.

The ratio term in equation (6) can be further simplified using a Taylor series of the exponential functions:

$$P_h(2f) \approx KP_0^2(f)\frac{[1 - \alpha_h(2f)z + 0.5(\alpha_h(2f)z)^2] - \begin{bmatrix} 1 - 2\alpha_f(f)z + \\ 0.5(2\alpha_f(f)z)^2 \end{bmatrix}}{2\alpha_f(f) - \alpha_h(2f)} \quad (7)$$

$$= KP_0^2(f)\frac{z(2\alpha_f(f) - \alpha_h(2f)) - 0.5z^2(2\alpha_f(f) - (\alpha_h(2f))(2\alpha_f(f) + (\alpha_h(2f)))}{2\alpha_f(f) - \alpha_h(2f)}$$

$$= KP_0^2(f)z[1 - 0.5z(2\alpha_f(f) + (\alpha_h(2f))]$$

$$\approx zKP_0^2(f)e^{\alpha_h(2f)z},$$

where the last step uses the common assumption ($\alpha_h(2f) = 2\alpha_f(f)$) and the Taylor series approximation.

In the case of a focused transmission using a clinical transducer array, $P_0(f)$ is modeled as:

$$P_0(f) = T(f)E_{tx}(f)D_{tx}(f) \quad (8)$$

where $T(f)$ is the transfer function of the transmit pulse, $E_{tx}(f)$ is the electro-mechanical transfer function on transmit, and $D_{tx}(f)$ is the diffraction patter on transmit. Using equations (7) and (8):

$$P_h(2f) = zKT^2(f)E_{tx}^2(f)D_{tx}^2(f)e^{-4\alpha_h(2f)z} \quad (9)$$

The Power Spectrum of the received second harmonic signal is given by:

$$S_h(2f) = P_h^2(2f)E_{rx}^2(2f)D_{rx}^2(2f)BSC(2f)e^{-4\alpha_h(f)z} \quad (10)$$

where $E_{rx}(f)$ is the electro-mechanical transfer function on receive, and $D_{rx}(f)$ is the diffraction patter on receive, $BSC(2f)$ is the backscatter coefficient (np/cm-str) at the second harmonic frequency, and $e^{-4\alpha_h(f)z}$ accounts for the attenuation of returned harmonic signal.

Combining equations (9) and (10):

$$S_h(2f) = [z^2T^4(f)E_{tx}^4(f)D_{tx}^4(f)E_{rx}^2(2f)D_{rx}^2(2f)]K^2BSC(2f)e^{-4\alpha_h(f)z} \quad (11)$$

In Tissue Harmonic Imaging (THI) mode, the radio-frequency signals from two pulses 180° out of phase are summed to obtain the harmonic signals.

Each radio-frequency echo line of the ROI is partitioned into several overlapping time gated windows. The Fourier Transform is applied to every window, and the power spectra of the windows that correspond to the same depth are averaged. The same procedure is performed on the corresponding ROI of the reference phantom.

The power spectra of the sample and reference in a ROI are given by equation (11). The term in brackets is assumed to be the same for both the sample and reference. By computing the ratio of the power spectrum from the sample and reference we obtain an equation similar to equation (3):

$$RS(2f, z) = \frac{S_{h,s}(2f)}{S_{h,r}(2f)} = \frac{K_s^2BSC_s(2f)e^{-4\alpha_s(2f)z}}{K_r^2BSC_r(2f)e^{-4\alpha_r(2f)z}} \quad (12)$$

Compensating for the known attenuation, backscatter, and nonlinearity of the reference phantom, equation (12) becomes:

$$RS'(2f,z) = K_s^2(f) BSC_s(2f) e^{-4\alpha_s(f)z} \quad (13)$$

Computing the natural logarithm yields:

$$\ln(RS'^{(2f,z)}) = \ln(K_s^2) + \ln(BSC_s(2f)) - 4\alpha_s(2f)z \quad (14)$$

The attenuation coefficient $\alpha_s$ (dB/cm) at frequency 2f can be derived from the slope of the line that fits equation (14) versus depth z. The intercept of the line that fits equation (14) versus depth z yields $\ln(BSC_s(2f))$ biased by the nonlinearity term $\ln(K_s^2)$.

Returning to process 200, a non-linearity of the ROI is determined at S270 based on the first BSC determined at S250 and the second BSC determined at S260. Continuing with the above example, the non-linearity term $\ln(K_s^2)$ in equation (14) can be estimated by measuring the $\ln(BSC_s(2f))$ using the fundamental frequency band based on equation (5), where the fundamental frequency is now 2f, and substituting the result into equation (14).

An image of the ROI is generated and displayed at S280. The image may be generated based on one or both of the spectra acquired at S230 as is known in the art. The image may also indicate the non-linearity and any other values determined based on the received signals.

Figure 5:
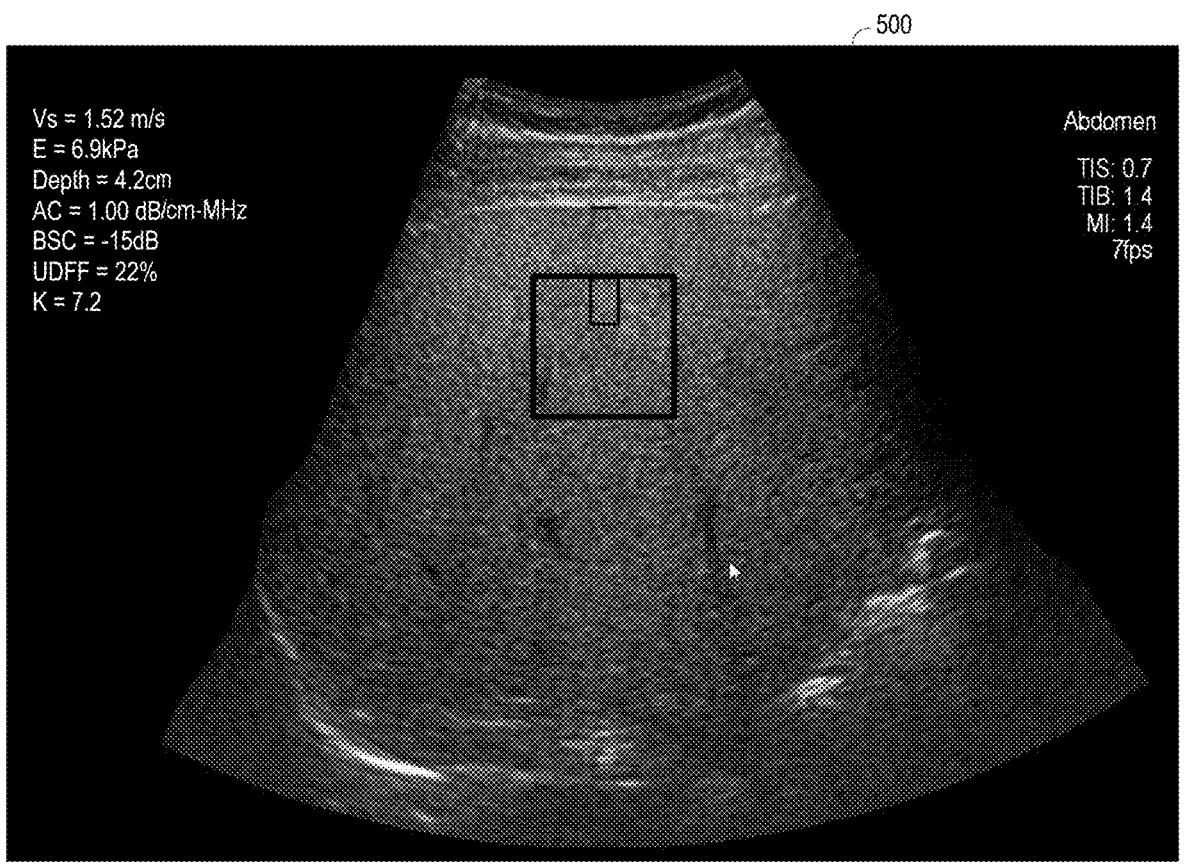
FIG. 5 is an ultrasound image including quantitative ultrasound values according to some embodiments.

FIG. 5 shows image 500 generated and displayed at S280 according to some embodiments. As shown, determined values shear wave speed (Vs), Elasticity (E), AC, BSC, ultrasonically-derived fat fraction (UDFF) and non-linearity (K) are displayed contemporaneously with ultrasound B-mode image data. These quantitative measurements may improve the diagnostic capability of medical ultrasound by removing the qualitative interpretation of B-mode images, and by reducing system-dependent factors.

The estimates of the AC based on the fundamental band and the harmonic band should be equivalent. Accordingly, image 500 may display either estimate or an average of the two. In some embodiments, variability may be reduced by determining and displaying a weighted average of the two AC estimates.

In the case of the BSC, the BSC value determined at S260 based on the harmonic band is biased by the nonlinearity term. Therefore, the BSC displayed at S280 may be the BSC value determined at S250 based on the fundamental band. If the nonlinearity term is assumed to be negligible, then an average of the two BSC values may be displayed.

Figure 6:
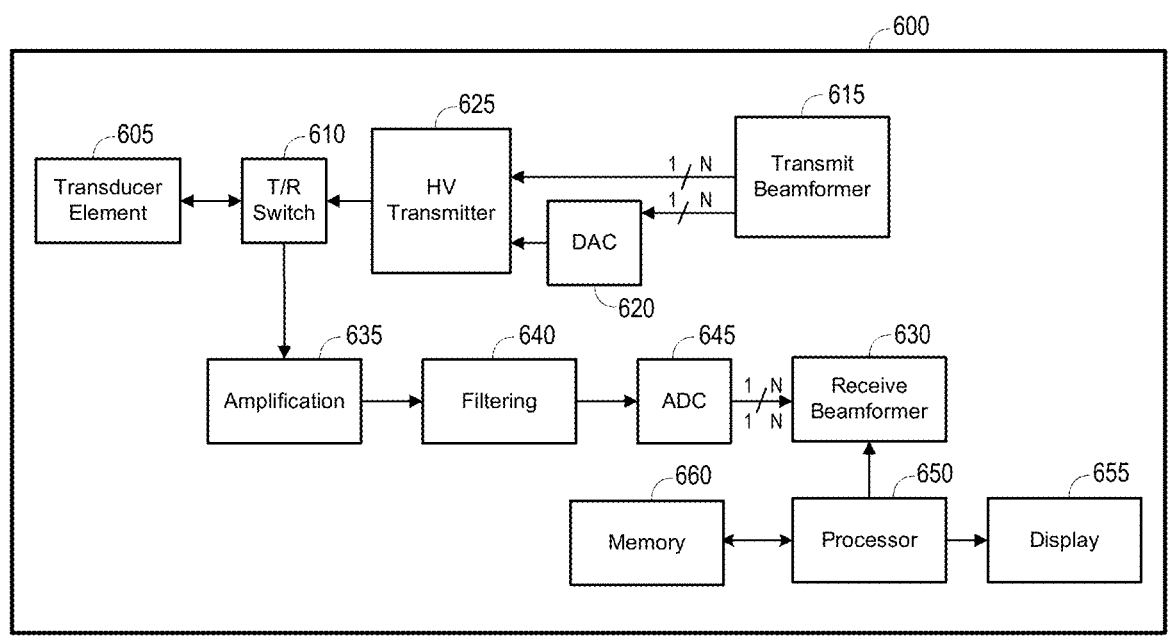
FIG. 6 is a block diagram of an ultrasound system according to some embodiments.

FIG. 6 is a block diagram of ultrasound imaging system 600 according to some embodiments. System 600 may implement one or more of the processes described herein.

System 600 is a phased-array ultrasound imaging system, but embodiments are not limited thereto. Typical phased array systems utilize 64 to 256 receive channels and a comparable number of transmit channels. For clarity, FIG. 6 illustrates a single transmit-and-receive channel.

System 600 comprises transducer element 605 and transmit/receive switch 610. Transducer element 605 may comprise an element of a 1-, 1.25-, 1.5-, 1.75- or 2-dimensional array of piezoelectric or capacitive membrane elements. Transmit/receive switch 610 is operated to either allow transmission of ultrasonic energy via element 605 (e.g., in response to application of a voltage across element 605), or to allow reception of a voltage generated by element 605 in response to received ultrasonic energy (i.e., echoes).

Transmit beamformer 615 is operable in conjunction with digital-to-analog converter 620 and high-voltage transmitter 625, to generate waveforms for a plurality of channels, where each waveform may exhibit a different amplitude, delay, and/or phase. Receive beamformer 630 receives signals from a plurality of channels, each of which may be subjected to amplification 635, filtering 640, analog-to-digital conversion 645, delays and/or phase rotators, and one or more summers. Receive beamformer 630 may be configured by hardware or software to apply relative delays, phases, and/or apodization to form one or more receive beams in response to each transmit beam. Receive beamformer 630 may provide dynamic receive focusing as is known in the art, as well as fixed focus reception.

The receive beams formed by receive beamformer 630 represent the material through which the transmit beams and receive beams have passed. The receive beams are output to processor 650 for processing. For example, processor 650 may generate images based on the receive beams.

Processor 650 may execute processor-executable program code stored in memory 660 to perform and/or to control other components of system 600 to perform the processes described herein. Processor 650 may comprise a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof, or other currently-known or later-developed device for generating data (e.g., image data) based on beamformed ultrasound samples.

Memory 660 may comprise a non-transitory computer readable storage media such as Random Access Memory and/or non-volatile memory (e.g., Flash memory, hard disk memory). Memory 660 may store program code, calibration data, B-mode images, and/or any other suitable data. Display 655 may comprise a cathode ray tube display, liquid crystal display, light-emitting diode display, plasma display, or other type of display for displaying images and/or measured values.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. An ultrasound system comprising:
    a memory storing an echo signal power spectrum of a reference phantom for a fundamental frequency band and an echo signal power spectrum of the reference phantom for a harmonic frequency band, wherein a center frequency of the harmonic frequency band is substantially similar to a center frequency of the fundamental frequency band;
    a transducer to:
        transmit first ultrasound beams into a region of tissue and receive first acoustic radio-frequency signals representing an echo signal power spectrum of the region of tissue for the fundamental frequency band; and
        transmit second ultrasound beams into the region of tissue and receive second acoustic radio-frequency signals representing an echo signal power spectrum of the region of tissue for the harmonic frequency band;
    a processing unit to:
        determine a first backscatter coefficient based on the echo signal power spectrum of the region of tissue for the fundamental frequency band and the echo signal power spectrum of the reference phantom for the fundamental frequency band;

determine a value representing a second backscatter coefficient and a non-linearity term associated with the region of tissue based on the echo signal power spectrum of the region of tissue for the harmonic frequency band and the echo signal power spectrum of the reference phantom for the harmonic frequency band; and determine the non-linearity term associated with the region of tissue based on the first backscatter coefficient and the value; and a display to display the second backscatter coefficient, the non-linearity term, and a B-mode image of the region of tissue.

2. An ultrasound system according to claim 1, wherein the echo signal power spectrum of the reference phantom for the fundamental frequency band and the echo signal power spectrum of the region of tissue for the fundamental frequency band were acquired using substantially similar scan settings.

3. An ultrasound system according to claim 2, wherein the echo signal power spectrum of the reference phantom for the harmonic frequency band and the echo signal power spectrum of the region of tissue for the harmonic frequency band were acquired using substantially similar scan settings.

4. A system according to claim 1, the memory storing an echo signal power spectrum of a second reference phantom for the fundamental frequency band and an echo signal power spectrum of the second reference phantom for the harmonic frequency band, and the processing unit further to determine to use the echo signal power spectrum of the reference phantom for the fundamental frequency band for the determination of the first backscatter coefficient and the echo signal power spectrum of the reference phantom for the harmonic frequency band for the determination of the second backscatter coefficient, based on a correlation between the region of tissue and the reference phantom.

5. A system according to claim 4, the echo signal power spectrum of the reference phantom for the fundamental frequency band and the echo signal power spectrum of the reference phantom for the harmonic frequency band having been acquired using first scan settings, the memory storing a second echo signal power spectrum of the reference phantom for the fundamental frequency band and a second echo signal power spectrum of the reference phantom for the harmonic frequency band, the second echo signal power spectrum acquired using second scan settings, wherein the echo signal power spectrum of the region of tissue for the fundamental frequency band and the echo signal power spectrum of the region of tissue for the harmonic frequency band are acquired using third scan settings, and wherein the processing unit is to determine to use the echo signal power spectrum of the reference phantom for the fundamental frequency band and the echo signal power spectrum of the reference phantom for the harmonic frequency band for the determination of the first backscatter coefficient and the determination of the second backscatter coefficient, based on a correlation between the first scan settings and the third scan settings.

6. A system according to claim 1, the processing unit further to:

determine an attenuation coefficient of the region of tissue based on the echo signal power spectrum of the region of tissue for the harmonic frequency band, the echo signal power spectrum of the reference phantom for the harmonic frequency band, and an attenuation coefficient of the reference phantom.

7. A system according to claim 6, further comprising:
the display to simultaneously display the second backscatter coefficient, the attenuation coefficient of the region of tissue, the non-linearity term, and the B-mode image of the region of tissue.

8. A method comprising:

controlling an ultrasound system transducer to acquire an echo signal power spectrum of a region of tissue for a fundamental frequency band and an echo signal power spectrum of the region of tissue for a harmonic frequency band, wherein a center frequency of the harmonic frequency band is substantially similar to a center frequency of the fundamental frequency band;

determining a first backscatter coefficient based on the echo signal power spectrum of the region of tissue for a fundamental frequency band and an echo signal power spectrum of a reference phantom for the fundamental frequency band;

determining a value representing a second backscatter coefficient and a non-linearity term associated with the region of tissue based on the echo signal power spectrum of the region of tissue for the harmonic frequency band and an echo signal power spectrum of the reference phantom for the harmonic frequency band;

determining the non-linearity term associated with the region of tissue based on the first backscatter coefficient and the value; and displaying the second backscatter coefficient, the non-linearity term, and a B-mode image of the region of tissue.

9. A method according to claim 8, wherein the echo signal power spectrum of the reference phantom for the fundamental frequency band and the echo signal power spectrum of the region of tissue for the fundamental frequency band are acquired using substantially similar scan settings.

10. A method according to claim 9, wherein the echo signal power spectrum of the reference phantom for the harmonic frequency band and the echo signal power spectrum of the region of tissue for the harmonic frequency band were acquired using substantially similar scan settings.

11. A method according to claim 8, further comprising:

storing an echo signal power spectrum of a second reference phantom for the fundamental frequency band and an echo signal power spectrum of the second reference phantom for the harmonic frequency band, and determining to use the echo signal power spectrum of the reference phantom for the fundamental frequency band for the determination of the first backscatter coefficient and the echo signal power spectrum of the reference phantom for the harmonic frequency band for the determination of the second backscatter coefficient, based on a correlation between the region of tissue and the reference phantom.

12. A method according to claim 11, the echo signal power spectrum of the reference phantom for the fundamental frequency band and the echo signal power spectrum of the reference phantom for the harmonic frequency band having been acquired using first scan settings, further comprising:

storing a second echo signal power spectrum of the reference phantom for the fundamental frequency band and the second echo signal power spectrum of the reference phantom for a harmonic frequency band, the second echo signal power spectrum acquired using second scan settings, wherein the echo signal power spectrum of a region of tissue for the fundamental frequency band and the echo signal power spectrum of the region of tissue for the harmonic frequency band are acquired using third scan settings, and further comprising determining to use the echo signal power spectrum of the reference phantom for the fundamental frequency band for the determination of the first backscatter coefficient and the echo signal power spectrum of the reference phantom for the harmonic frequency band for the determination of the second backscatter coefficient, based on a correlation between the first scan settings and the third scan settings.

13. A method according to claim 8, further comprising:
determining an attenuation coefficient of the region of tissue based on the echo signal power spectrum of the region of tissue for the harmonic frequency band, the echo signal power spectrum of the reference phantom for the harmonic frequency band, and an attenuation coefficient of the reference phantom.

14. A method according to claim 13, further comprising:
simultaneously displaying the second backscatter coefficient, the attenuation coefficient of the region of tissue, the non-linearity term, and the B-mode image of the region of tissue.

15. An ultrasound imaging system comprising:
a transducer to acquire an echo signal power spectrum of a region of tissue for a fundamental frequency band and an echo signal power spectrum of the region of tissue for a harmonic frequency band, wherein a center frequency of the harmonic frequency band is substantially similar to a center frequency of the fundamental frequency band;
a processing unit to:
determine a first backscatter coefficient based on the echo signal power spectrum of the region of tissue for the fundamental frequency band and an echo signal power spectrum of a reference phantom for the fundamental frequency band;
determine a value representing a second backscatter coefficient and a non-linearity term associated with the region of tissue based on the echo signal power spectrum of the region of tissue for the harmonic frequency band and an echo signal power spectrum of the reference phantom for the harmonic frequency band; and
determine the non-linearity term associated with the region of tissue based on the first backscatter coefficient and the value; and
a display to display the second backscatter coefficient, the non-linearity term, and a B-mode image of the region of tissue.

16. A system according to claim 15, wherein the echo signal power spectrum of the reference phantom for the fundamental frequency band and the echo signal power spectrum of the region of tissue for the fundamental frequency band are acquired using substantially similar scan settings.

17. A system according to claim 15, the processing unit to determine to use the echo signal power spectrum of the reference phantom for the fundamental frequency band for the determination of the first backscatter coefficient and the echo signal power spectrum of the reference phantom for the harmonic frequency band for the determination of the second backscatter coefficient, based on a correlation between the region of tissue and the reference phantom.

18. A system according to claim 17, wherein the echo signal power spectrum of the reference phantom for the fundamental frequency band and the echo signal power spectrum of the reference phantom for the harmonic frequency band are acquired using first scan settings, wherein the echo signal power spectrum of a region of tissue for the fundamental frequency band and the echo signal power spectrum of the region of tissue for the harmonic frequency band are acquired using second scan settings, and wherein the processing unit is to determine to use the echo signal power spectrum of the reference phantom for the fundamental frequency band for the determination of the first backscatter coefficient and the echo signal power spectrum of the reference phantom for the harmonic frequency band for the determination of the second backscatter coefficient, based on a correlation between the first scan settings and the second scan settings.

* * * * *